United States Patent [19]

Farng et al.

[11] Patent Number: 5,169,547

[45] Date of Patent: Dec. 8, 1992

[54] AMINE-CONTAINING HINDERED PHENOLIC ANTIOXIDANT LUBRICANT ADDITIVES AND COMPOSITIONS THEREOF

[75] Inventors: Liehpao O. Farng, Lawrenceville; Andrew G. Horodysky, Cherry Hill, both of N.J.

[73] Assignee: Mobil Oil Corporation, Fairfax, Va.

[21] Appl. No.: 250,890

[22] Filed: Sep. 29, 1988

Related U.S. Application Data

[63] Continuation-in-part of Ser. No. 898,463, Aug. 20, 1986, abandoned.

[51] Int. Cl.$^5$ .................................. C10M 139/00
[52] U.S. Cl. ..................... 252/49.6; 558/292; 558/294; 558/295; 564/8; 564/9; 564/10; 564/11
[58] Field of Search .................. 564/8, 9, 10, 11; 558/294, 295; 252/49.6

[56] References Cited

U.S. PATENT DOCUMENTS

| | | | |
|---|---|---|---|
| 3,347,793 | 10/1967 | Washburn et al. | 252/49.6 |
| 3,356,707 | 12/1967 | Hinkamp et al. | 260/462 |
| 3,359,298 | 12/1967 | Hunter et al. | 260/462 |
| 3,697,574 | 10/1972 | Piasek et al. | 546/9 |
| 3,704,308 | 11/1972 | Piasek et al. | 564/9 |
| 4,016,092 | 4/1977 | Andress | 252/32.5 |
| 4,132,702 | 1/1979 | Schmidt et al. | 260/45.8 N |
| 4,474,670 | 10/1984 | Braid et al. | 252/32.7 |
| 4,507,216 | 3/1985 | Braid et al. | 252/49.6 |
| 4,530,770 | 7/1985 | Braid | 252/49.6 |

FOREIGN PATENT DOCUMENTS 631434 11/1961 Canada .................. 558/294

*Primary Examiner*—Ellen McAvoy
*Attorney, Agent, or Firm*—Alexander J. McKillop; Charlesd J. Speciale; Howard M. Flournoy

[57] ABSTRACT

Borated or partially borated, amine-contained hindered phenols provide effective antioxidant properties to compositions comprising lubricants and liquid fuels.

18 Claims, No Drawings

AMINE-CONTAINING HINDERED PHENOLIC ANTIOXIDANT LUBRICANT ADDITIVES AND COMPOSITIONS THEREOF

This application is a continuation-in-part of Ser. No. 898,463, filed Aug. 20, 1986, which is now abandoned.

BACKGROUND OF THE INVENTION

The use of borate esters of hindered phenols, i.e. phenols in which both ring positions ortho to the hydroxy group have been substituted by bulky hydrocarbyl groups, is known in the art for their antioxidant and antifatigue properties in a variety of products including lubricating oils, greases, and fuels. U.S. Pat. No. 3,347,793, for example, teaches certain 2,6-di-t-alkylphenyl borates as oil additives. U.S. Pat. Nos. 3,356,707, and 3,359,298 disclose similar compositions.

The use of arylamines, such as alkylated diphenylamines, p-phenylenediamines, have been well known for their antioxidant properties in a variety of products including polymers and lubricants.

The use of hindered phenols containing a polar amine-substituent with desirable surface-active properties has proven valuable in many types of industrial oils; antirust protection is improved, and inherent dispersancy characteristics help lengthen maintenance periods by inhibiting the deposition of harmful deposits. A good example is Ethanox 703 (2,6-t-butyl-$\alpha$-dimethylamino-p-cresol) commercially available from Ethyl Corporation.

It has now been found that the use of the novel borate esters of amine-containing hindered phenols in accordance with this invention provide exceptional antioxidant activity, with the multifunctional potential of antifatigue, antirust, and antiwear properties.

SUMMARY OF THE INVENTION

This invention is directed to compositions comprising a major amount of an oil of lubircating viscosity or grease prepared therefrom or liquid fuel, and a minor multifunctional amount of a borate of an amine containing hindered phenol prepared by boronating both the phenolic hydroxy group and the amine group of a para-nitrogenous hindered phenol.

These remarkable benefits can be utilized for a variety of synthetic and mineral oil based lubricants. The compositions of matter, i.e., products, and the lubricant compositions containing them are believed to be novel. To the best of our knowledge, these compositions have not been previously used in lubricating oils, greases, or fuel applications.

DESCRIPTION OF PREFERRED EMBODIMENTS

Lubricant compositions containing small additive concentrations of borate esters of para-substituted, amine containing, hindered phenols, such as 2,6-di-t-butyl-$\alpha$-dimethylamino-p-cresol borate, possess excellent antioxidant activity. Both the borate ester groups and the para-substituted amine or hydrocarbylene groups are believed to provide the basis for improved antioxidant activity. The polar amino group is also believed to contribute additional surface-active properties to the additives. Not only does it prolong the oxidation life of a lubricant, it will also impart alkalinity, dispersancy, antirust, antifatigue, and antiwear properties to the lubricant. These beneficial properties are believed to be enhanced as a result of novel internal synergism. This multifunctional/multipurposed additive concept is believed to be applicable to similar structures containing both (a) a borate ester of hindered phenol, and (b) an amine-containing, para-substituted groups within the same molecule.

Generally speaking, the para-nitrogenous, hindered phenols are converted to their corresponding borates by reaction in substantially equimolar amounts with a borating agent. The reaction mixture is refluxed under a nitrogen blanket and inert media until the ceasing of evolution of water (e.g., in a Dean Stark trap). The product is then freed from solvent by stripping under reduced pressure.

The borating agent which is reacted with the hindered phenol is any suitable borating agent known in the art, as for example, boric oxide or a compound of the formula

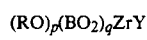

$$(RO)_p(BO_2)_q ZrY$$

where R, Y, and Z are hydrogen or alkyl groups containing 1 to about 6 carbon atoms, p and r are 0 to 2, and q is 1 to 3 or.

The useful boronating compounds covered by the above formula include boric acid, metaboric acid, alkyl metaborates, alkyl boroxines, boroxine boroxides, and the like, as well as alkyl borates.

The para-nitrogenous, hindered phenols that are contemplated have the formula

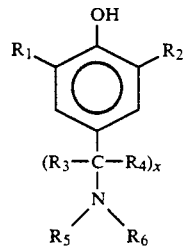

where $R_1$ and $R_2$ are the same or different alkyl groups containing from 1 to about 18 carbon atoms, or hydrogen (with the proviso that both $R_1$ and $R_2$ can not be hydrogen at the same time); $R_3$ and $R_4$ are hydrogen, or hydrocarbyl, aralkyl, or cycloalkyl groups, $R_5$ and $R_6$ are hydrogen, or hydrocarbyl, aralkyl, cycloalkyl, aryl, or alkylaryl groups and x is from 0 to about 12 and $R_3$, $R_4$, $R_5$, $R_6$ can contain from 1 to about 20 carbon atoms. However, any phenol which has alkyl groups of 1 to about 18 carbon atoms in the two positions ortho to the hydroxyl group can be used in the preparation of the borate esters of this invention.

Either the phenolic hydroxyl group and/or the amine group may be borated in the practice of this invention. Thus, the products of this invention may include boration of both of the active moieties within the same molecule via internal synergism.

Although the liquid hydrocarbons primarily improved by the novel borate esters disclosed herein are oils of lubricating viscosity or greases prepared therefrom, liquid hydrocarbon fuels such as distillate fuels or gasoline can also be improved in accordance with this invention. The additive products of the present invention are also useful in alcoholic fuels, gasohol and mixtures thereof.

The use of additive concentrations as low as 0.01% and up to about 10 wt. %, preferably 0.1–5 wt. % and more preferably 0.3–1% of borate esters of the amine-containing, para-substituted, hindered phenols in premium quality automotive and industrial lubricants will significantly enhance their stability and extend their service life. Fuel compositions can contain as little as 1 pound additive per 1,000 barrels of fuel and up to 500 pounds/1,000 barrels of fuel.

In general, mineral oils when employed as lubricant or grease vehicles, may be of any suitable lubricating viscosity range, as for example, from about 45 SSU at 100° F. to about 6000 SSU at 100° F. and preferably from about 50 SSU at 210° F. to about 250 SSU at 210° F. These oils may have viscosity indices varying from below 0 to about 100 or higher. The average molecular weights of these oils may range from about 250 to about 800. In grease formulation, the lubricating oil is generally employed in an amount sufficient to balance the total grease composition after accounting for the desired quantity of the thickening agent and other additive components to be included in the grease formulation. Thickening agents include soap-thickeners such as lithium hydroxystearate thickeners, calcium stearate thickeners, and other useful thickeners which include clay thickeners. In instances where synthetic oils are desired in preference to mineral oils as lubricant or as the vehicle for grease, or in combinations with mineral oils, a variety of synthetic oils can be used. Typical synthetic lubricants or grease vehicles include polyisobutylene, polybutenes, hydrogenated polydecenes, polypropylene glycol, polyethylene glycol, trimethylol propane esters, neopentyl and pentaerythritol esters, di(2-ethylhexyl)sebacate, di(2-ethylhexl)adipate, dibutyl phthalate, fluorocarbons, silicate esters, silanes esters of phosphorus-containing acids, liquid ureas, ferrocene derivatives, hydrogenated mineral oils, chain-type polyphenyls, siloxanes and silicones (polysiloxanes), alkyl-substituted diphenyl ethers typified by a butyl-substituted bis(p-phenoxy phenyl)ether, phenoxy phenylethers, etc.

It is to be understood also that the compositions contemplated herein can contain other additive materials. For example, antiwear additives such as metallic (zinc) dithiophosphates, antioxidants, corrosion inhibitors, extreme pressure agents such as sulfurized olefins, viscosity index agents such as polymers, and fillers can be used. Among such materiala are colloidal silica, calcium acetate, calcium carbonate and molybdenum disulfide. Such additives or characterizing materials do not detract from the lubricating value of the compositions of this invention, nor do they detract from the beneficial character of the borates of this invention; rather, these materials serve to impart their customary properties to the particular compositions into which they are incorporated.

The invention having been described in general terms, the following examples are specific embodiments thereof which, however, are intended not to limit the scope of this specification or the claims.

EXAMPLE 1

2,6-di-tertiary-butyl-dimethylamino-p-cresol borate

A mixture of 2,6-di-tertiary-butyl-dimethylamino-p-cresol (131.5 gm, 0.5 mole), boric acid (31.0 gm, 0.5 mole), and benzene (450 ml.) was heated while stirring vigorously at 85° C. for twenty-two hours. Water (5.5 ml.) formed during reaction was collected by azeotropic distillation. At the end of the reaction, the unreacted, insoluble material was removed by filtration, and the benzene was removed under reduced pressure using a rotary evaporator. This gave a golden orange solid (129.5 gm) with a melting point of 75°–80° C.

EXAMPLE 2

2,6-di-tertiary-butyl-dimethylamino-p-cresol borate

A mixture of 2,6-di-tertiary-butyl-dimethylamino-p-cresol (263 gm, one mole), boric acid (20.7 gm, 0.33 mole), and toluene (650 ml.) was heated while stirring vigorously at 115° C. for four hours and water (6.5 ml.) was collected by azeotropic distillation. At the end of the reaction, the unreacted, insoluble material was removed by filtration, and the toluene was removed under reduced pressure, leaving the product as a golden orange solid (258 gm) with a melting point of 73°–79° C.

EXAMPLE 3

Hindered Phenol-derived Mannich Diborates

Approximately 102 grams of distilled cocoamine, commerically obtained, 43 grams aqueous formalin (37% aqueous formaldehyde), and 150 milliliters of methanol were placed in a one-liter flask under agitation. Then 103 grams 2,6-ditert-butylphenol was added at ambient temperature. The reaction mixture was heated at reflux methanol for one hour. Thereafter, the volatiles (methanol and water) were removed since 70° C. to 115° C. at reduced pressure. Upon cooling to 65° C., 92 grams 1,2-epoxydodoecane (Vikolox 12 commercially obtained from Viking Chemical Company) were added. This mixture was reacted at 100° C. for 2.5 hours. Thereafter, 30.9 grams of boric acid and about 300 milliliters of toluene were charged into the reactors, and the boration was conducted at 100°–115° C. The water was collected by azeotropic distillation. At the end of the reaction, the unreacted, insoluble material was removed by filtration, and the toluene was removed by vacuum distillation. This gave a dark fluid weighing 259 grams.

The products of Examples 1 and 2 were blended into fully formulated oils and evaluated by catalytic oxidation test at 325° F. for forty hours with the results shown in Table 1. A comparison of the oxidation-inhibiting characteristics of this product with the other hindered phenols and hindered phenyl borates in fully formulated oils is also included in Table 1.

Catalytic Oxidation Test

Samples of the test lubricants were placed in an oven at 325° F. The samples were in the presence of the following metals known to catalyze organic oxidation:
 a. 15.6 sq. in. of sand blasted iron wire
 b. 0.78 sq. in. of polished copper wire
 c. 0.87 sq. in. of polished aluminum wire
 d. 0.167 sq. in. of polished lead surface.

Dry air was passed through the test samples at a rate of about 5 liters per hour for 40 hours.

TABLE 1

| | Catalytic Oxidation Test | | | |
| Item | Additive Conc. (Wt. %) | Sludge Rating | Change in Acid Value | % Increase in Viscosity |
| --- | --- | --- | --- | --- |
| 1 Base oil (150 second, | — | Nil | 2.58 | 30.61 |

TABLE 1-continued

| | Catalytic Oxidation Test | | | |
|---|---|---|---|---|
| Item | Additive Conc. (Wt. %) | Sludge Rating | Change in Acid Value | % Increase in Viscosity |
| fully formulated, solvent refined paraffinic bright oil containing defoamant/demulsifier/ antiwear/anticorrosion/ EP/antirust performance package) | | | | |
| 2 2,6-di-t-butyl- -dimethyl-amino-p-cresol borate (Ex. 1) | 0.5 | Nil | −0.74 | 6.06 |
| 3 2,6-di-t-butyl-p-cresol borate (DBPC borate) | 0.5 | Nil | 0.98 | 25.64 |
| 4 2,6-di-t-butyl-4-hydroxy-phenyl borate (Ethyl 701 borate) | 0.5 | TR | 1.00 | 26.21 |
| 5 2,6-di-t-butyl- -dimethyl-amino-p-cresol | 0.5 | TR | 0.70 | 26.63 |
| 6 2,6-di-t-butyl-p-cresol | 0.5 | TR | 1.82 | 32.35 |
| 7 2,6-di-t-butyl phenol | 0.5 | MOD | 1.34 | 30.70 |

The addition of the product of Example 1 at 0.5% concentration to a fully formulated mineral oil based gear oil controls the increase in viscosity of the test oil much better than equal concentrations of more traditional hindered phenolic antioxidants and other prior art hindered phenyl borates. Non-nitrogenous hindered phenyl borates are much poorer in control of viscosity during oxidation than are the subject compositions of this patent application as shown by Items 3–4 of Table 1. These novel compositions described in this patent application are highly useful at low concentrations and do not contain any patentably undesirable phosphorus or sulfur. Furthermore, the data contained in the Table 1 clearly demonstrate the superior performance of the amine-containing hindered phenols disclosed herein.

Example 1 performs significantly better than the unborated species (Item 5) and better than a well-known commercial antioxidant (Item 4). In fact Example 1 has better across the board performance than any of the prior art materials compared in Table 1.

The product of Example 3 was blended (1) into a fully formulated mineral and (2) into a fully formulated ester oil and evaluated for oxidative stability in accordance with a procedure using differential scanning calorimetry. See the article by F. Noel and G. E. Cranton in Analytical Calorimetry, Vol. 3, pages 305–320 (1974) "Application of Scanning Calorimetry to Petroleum Oil Oxidation Studies". The on-set of oxidation was measured for each sample indicated See Table 2 below.

TABLE 2

Differential Scanning Calorimetry
Equilibrate at 30° C. and Increase 10° C./Minute to
300° C. Measure the On-Set Temperature for
the Beginning of Oxidation

| Item | On-Set Temperature |
|---|---|
| Base Oil (200 second, solvent refined paraffinic neutral, mineral oil) | 181.7° C. |
| 1% of Example 3 | 229.2° C. |
| 2% of Example 3 | 263.7° C. |
| Base Oil (pentaerythritol derived synthetic esters) | 192.9° C. |
| 1% of Example 3 | 275.4° C. |

As shown above, the product of Example 3 in accordance with this invention shows considerable antioxidant property improving (retarding) the oxidative stability of lubricating oils from about 47° to about 82° C. at concentrations of only 1%.

Although this present invention has been described with preferred embodiments, it is to be understood that modifications and variations may be resorted to, without departing from the spirit and scope of this invention, as those skilled in the art will readily understand. Such modifications and variations are considered to be within the purview and scope of the appended claims.

What is claimed is:

1. An improved lubricant composition comprising a major amount of an oil of lubricating viscosity or grease prepared therefrom and a minor multifunctional antioxidant, antirust, antifatigue, antiwear amount of from about 0.01 to about 10 wt % based on the total weight of the composition of a borate of an amine-containing hindered phenol prepared by boronating both the phenolic hydroxyl group and the amine group of a para-nitrogenous hindered phenol having the below described generalized formula

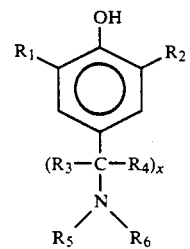

where $R_1$ and $R_2$ are the same or different alkyl groups containing 1 to about 18 carbon atoms, or hydrogen; $R_3$ and $R_4$ are hydrogen, or hydrocarbyl, aralkyl, or cycloalkyl groups containing from 1 to about 20 carbon atoms; $R_5$ and $R_6$ are hydrogen, or hydrocarbyl, aralkyl, cycloalkyl, aryl or alkylaryl groups containing from 1 to about 20 carbon atoms, with the proviso that $R_1$ and $R_2$ cannot both be hydrogen at the same time and x is 0, 1 or 2.

2. The composition of claim 1 wherein said phenol is 2,6-di-t-butyl-dimethylamino-p-cresol.

3. The composition of claim 1 wherein the phenol is prepared from cocoamine and 2,6-di-tert-butylphenol.

4. The composition of claim 1 wherein said boronating agent is a compound having the generalized formula $$(RO)_p(BO_2)_q ZrY$$

where R, Y, and Z are hydrogen or alkyl groups containing 1 to about 6 carbon atoms, p and r are 0 to 2, and q is 1 to 3.

5. The composition of claim 1 wherein the boronating agent is selected from the group consisting of boric oxide, boric acid, metaboric acid, and boroxine boroxides.

6. The composition of claim 5 wherein the boronating agent is boric acid.

7. The composition of claim 1 wherein the oil of lubricating viscosity is selected from mineral and synthetic oils or mixtures thereof.

8. The composition of claim 7 wherein said oil is a mineral oil.

9. The composition of claim 7 wherein said oil is a synthetic oil.

10. The composition of claim 1 wherein said major proportion is a grease.

11. An improved additive product of reaction suitable for use as a multifunctional antioxidant, antirust, antifatigue, antiwear agent in lubricant compositions consisting of a borate of an amine-containing hindered phenol prepared by boronating both the phenolic hydroxyl group and the amine group of a para-nitrogenous hindered phenol having the below described generalized formula

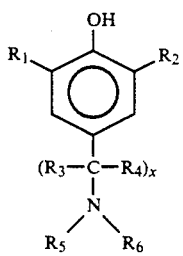

where $R_1$ and $R_2$ are the same or different alkyl groups containing from 1 to about 18 carbon atoms, or hydrogen; $R_3$ and $R_4$ are hydrogen or hydrocarbyl, aralkyl, or cycloalkyl groups, containing from 1 to about 20 carbon atoms, $R_5$ and $R_6$ are hydrogen, or hydrocarbyl, aralkyl, cycloalkyl, aryl or alkylaryl groups containing from 1 to about 20 carbon atoms, with the proviso that $R_1$ and $R_2$ cannot both be hydrogen at the same time and x is 0, 1 or 2.

12. The product of claim 11 wherein the boronating agent is a compound having the generalized formula $$(RO)_p(BO_2)_q ZrY$$

where R, Y, and Z are hydrogen or alkyl groups containing 1 to about 6 carbon atoms, p and r are 0 to 2, and q is 1 to 3.

13. The product of claim 11 wherein the boronating agent is selected from boric oxide, boric acid, metaboric acid, and boroxine boroxides.

14. The product of claim 13 wherein the boronating agent is boric acid.

15. The product of claim 11 wherein said phenol is 2,6-di-tert-butyl-dimethylamino-p-cresol.

16. The product of claim 11 wherein said phenol is prepared from cocoamine and 2,6-di-tert-butylphenol.

17. A method of improving the oxidation stability of a composition consisting essentially of oils of lubricating viscosity, or greases prepared therefrom comprising adding minor antioxidant amounts of an additive product as described in claim 11.

18. The method of claim 17 wherein from about 0.01 to about 10 wt % based on the weight of the total compositions of said additive product is added thereto.

* * * * *